US008177754B2

(12) United States Patent
Barnes

(10) Patent No.: US 8,177,754 B2
(45) Date of Patent: May 15, 2012

(54) SURGICAL PORT SEAL

(75) Inventor: Andrew L. Barnes, Naugatuck, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/701,770

(22) Filed: Feb. 8, 2010

(65) Prior Publication Data

US 2010/0241078 A1     Sep. 23, 2010

Related U.S. Application Data

(60) Provisional application No. 61/161,450, filed on Mar. 19, 2009.

(51) Int. Cl.
*A61M 5/178* (2006.01)
(52) U.S. Cl. .................................. 604/167.01
(58) Field of Classification Search ............ 604/167.01, 604/167.02, 167.04, 533–537, 167.03, 167.06, 604/168.01; 251/149.1
See application file for complete search history.

(56) References Cited

U.S. PATENT DOCUMENTS

| | | | | |
|---|---|---|---|---|
| 3,967,645 A | * | 7/1976 | Gregory | 137/846 |
| 4,341,239 A | * | 7/1982 | Atkinson | 137/493 |
| 4,436,519 A | * | 3/1984 | O'Neill | 604/175 |
| 5,456,284 A | | 10/1995 | Ryan et al. | |
| 5,492,304 A | * | 2/1996 | Smith et al. | 251/149.1 |
| 6,024,729 A | * | 2/2000 | Dehdashtian et al. | 604/256 |
| 2003/0085373 A1 | * | 5/2003 | Dehdashtian | 251/149.3 |
| 2007/0244426 A1 | | 10/2007 | Hart et al. | |

FOREIGN PATENT DOCUMENTS

| | | |
|---|---|---|
| EP | 0630660 A1 | 12/1994 |
| EP | 0873721 A2 | 10/1998 |
| EP | 1759645 A1 | 3/2007 |

OTHER PUBLICATIONS

Extended European Search Report dated Jun. 24, 2010 issued by the European Patent Office in counterpart EP Application No. EP 10 250 510.4.

* cited by examiner

*Primary Examiner* — Christopher D Koharski

(57) ABSTRACT

A seal device having a substantially conical shape including a slit opening at its tip defined by a pair of planar surfaces, the opening reinforced by gussets on the exterior surface of the seal device and adjacent to the end regions of the slit. The gussets help bias the ends of the slit towards a closed position, even when an instrument is located within the slit, to thereby reduce "cat-eye"-ing and minimize leakage therethrough. The seal device may include ramps on respective inner surfaces of the device, the ramps functioning as a lead-in to the slitted opening such an inserted instrument contacts the ramps first and opens the slit prior to the instrument contacting the material of the slit. Along the outer surface of the device is a flexible body portion to minimize the effect on the opening when an instrument is inserted into the device.

10 Claims, 4 Drawing Sheets

SURGICAL PORT SEAL

CROSS REFERENCE TO RELATED APPLICATION

The present application claims the benefit of and priority to U.S. Provisional Application Ser. No. 61/161,450 filed on Mar. 19, 2009, the entire contents of which are incorporated herein by reference.

BACKGROUND

1. Technical Field

The present disclosure relates to a fluid seal for an arthroscopic cannula to seal off a surgical worksite when elongated arthroscopic instruments are inserted through the cannula as well as when no instrument is present in the cannula.

2. Background of Related Art

Arthroscopic and other endoscopic surgical procedures facilitate minimally invasive surgical procedures in which elongated instruments inserted through small incisions in a patient's body are inserted into a body cavity. Arthroscopic procedures often require the use of pressurized fluid to distend and irrigate the body cavity. Therefore, seals have been devised for cannula used in these procedures to minimize the uncontrolled loss of irrigating fluid from the body cavity.

As instruments are inserted and manipulated in the seal, leakage of gases or fluids may occur. The known seals are deficient in numerous ways, including an inability to accommodate a wide range of instrument size and an inability to preserve the integrity of the seal during the procedure.

SUMMARY

The present disclosure is sometimes described herein in the context of an arthroscopic surgical procedure; however, it should be recognized that the present invention may be equally applicable to any type of surgical procedure, e.g., arthroscopic, endoscopic, laparoscopic, thoracic, etc. and that the present invention is intended to cover devices suitable for use in any one or more of such surgical procedures. The present invention is particularly well-suited for arthroscopic applications, in which sutures are often present and which may affect the ability of a seal arrangement to effectively create a seal around an instrument.

In an embodiment, the present invention describes a fluid seal for a surgical, e.g., arthroscopic, cannula to seal off a surgical worksite both when an elongated surgical, e.g., arthroscopic, instrument is inserted through the cannula and when no instrument is present. In one embodiment of the present disclosure, a port having a duckbill seal is described. Within the port are ramps, which act as lead-ins to open a slit in the duckbill seal prior to the slit coming in contact with an instrument. Gussets on the outside of the port press against the slit to add extra support and improve the quality of the seal.

BRIEF DESCRIPTION OF THE DRAWINGS

By way of description only, embodiments of the disclosure will be described with reference to the accompanying drawings, in which.

DETAILED DESCRIPTION OF THE EMBODIMENTS

Figure 1:
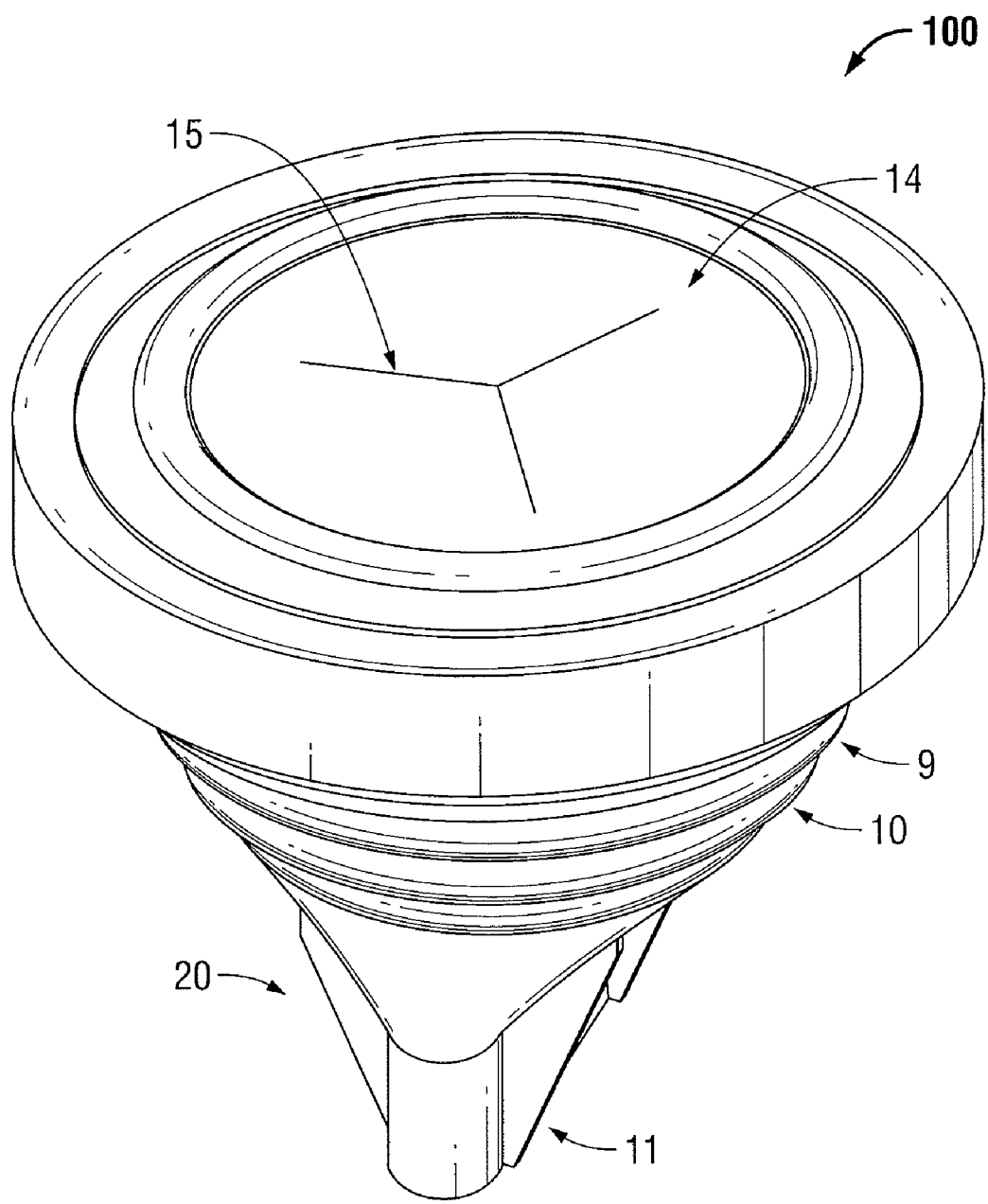
FIG. 1 is a top perspective view showing an arthroscopic port seal according to the present disclosure.

Particular embodiments of the present disclosure will be described herein with reference to the accompanying drawings. As shown in the drawings and as described throughout the following descriptions, and is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

The seal device 100 is adapted for use with a trocar assembly, including an obturator and a cannula, and is utilized for minimally invasive, such as endoscopic, arthroscopic or laparoscopic etc., procedures. The seal device 100 cooperates with the obturator or other instruments extending through the cannula to form a seal around the outer surface of the instrument and reduce, minimize or preclude the passage of fluids through the body cavity and trocar assembly.

An embodiment of a seal device 100 is shown in FIGS. 1 to 4. The seal device 100 allows for the introduction and manipulation of a variety of instruments adapted for insertion through a trocar or cannula assembly while preserving the atmospheric integrity of the body cavity from gas or fluid leakage. Examples of instrumentation used in such procedures includes, but is not limited to, clip appliers, graspers, dissectors, retractors, staplers, laser probes, photogenic devices, endoscopes and laparoscopes, tubes and the like. Such instruments will be collectively referred to herein as "instruments or instrumentation".

The seal device 100, as depicted in FIG. 1, includes a generally elongated conical body portion 20 and is outfitted with an elastomeric membrane 14 having slits 15 in its surface to permit the insertion of instrumentation (not shown) located at the proximal end of the seal device 100.

In one embodiment, shown in FIG. 1, the elastomeric membrane 14 is disposed within the conical body portion 20. In an embodiment, the elastomeric membrane 14 has a slightly larger diameter than the inner diameter of the conical body portion. This causes the conical body portion 20 to deform slightly and form a tight seal around the membrane when so engaged. In an embodiment, the slits 15 are arranged as three slits sharing a common center point with each slit equidistant from each other. It is envisioned that this configuration will tightly seal the instrumentation while allowing for manipulation of the instrumentation.

Figure 2:
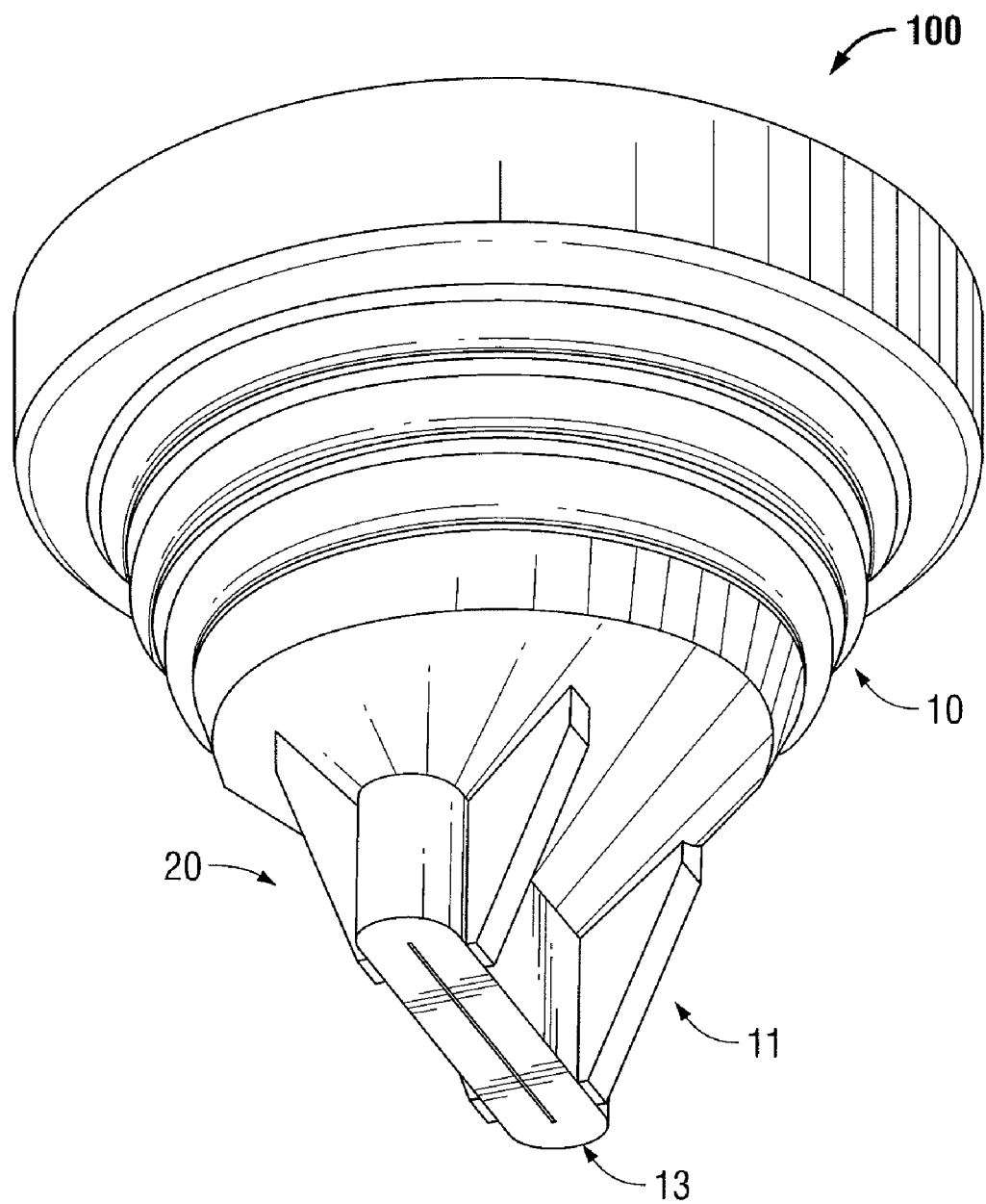
FIG. 2 is a bottom perspective view showing the arthroscopic port seal of FIG. 1.
Figure 3:
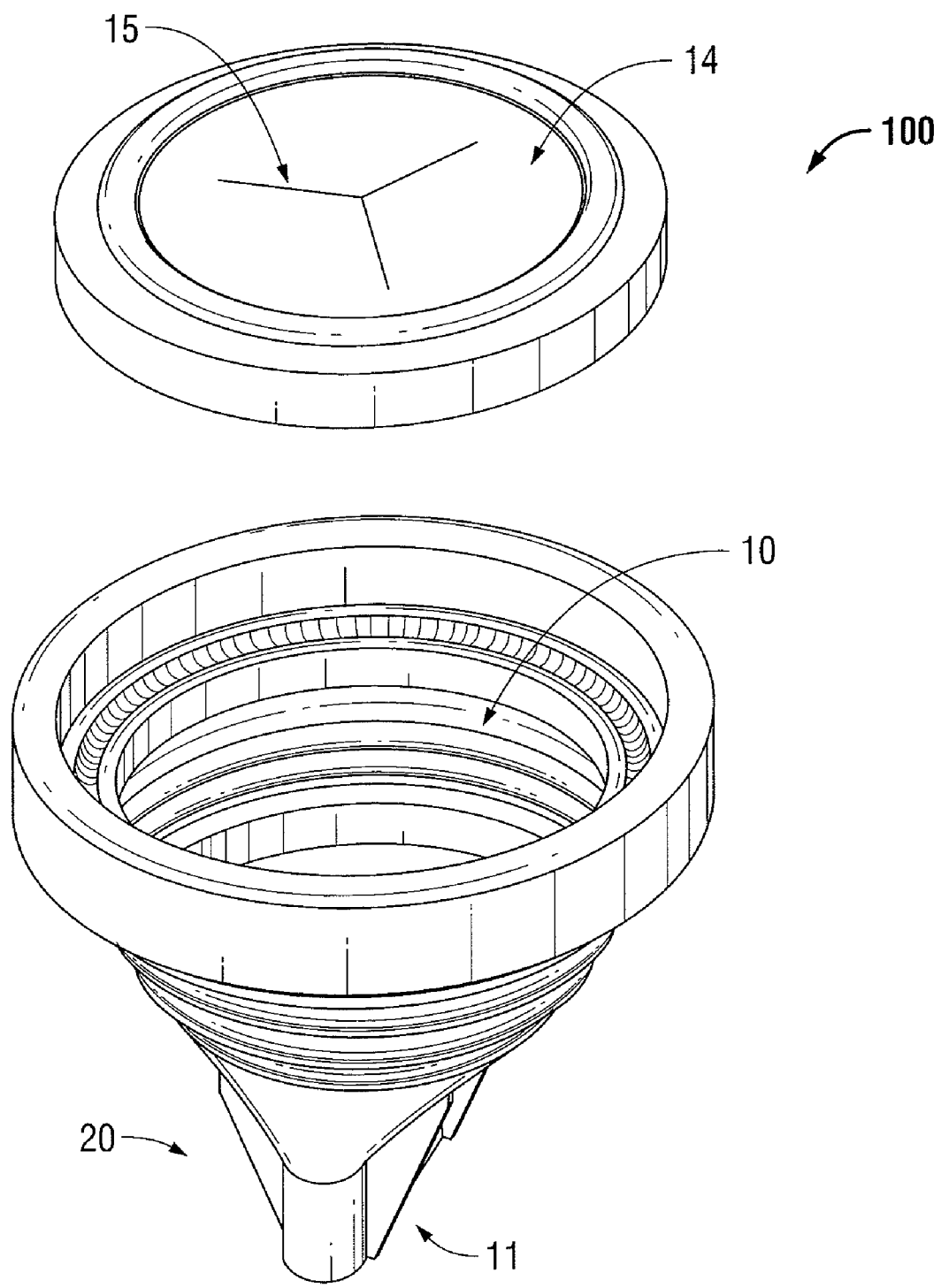
FIG. 3 is an exploded perspective view of the arthroscopic port seal of FIG. 1.
Figure 4:
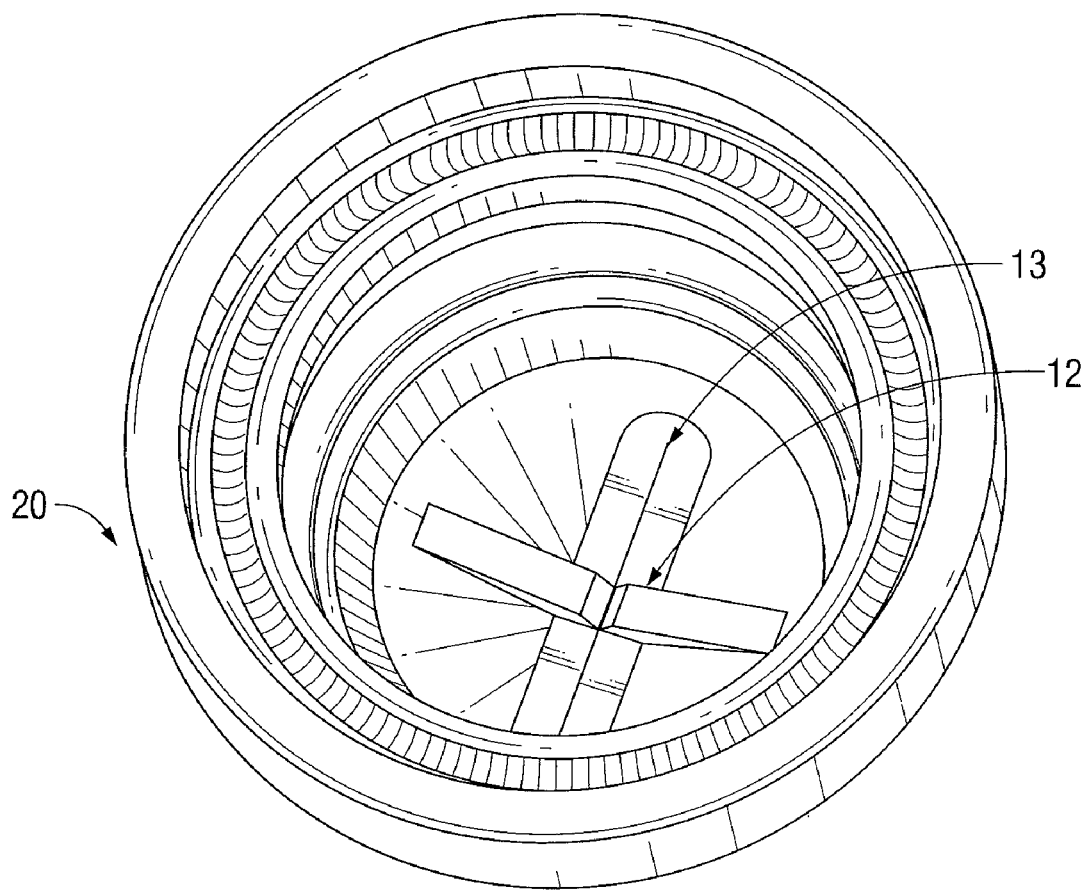
FIG. 4 is a top view of the arthroscopic port of FIG. 1.

The conical body portion 20 of the seal device 100 may have a body portion 10, as shown in FIG. 2. The body portion 10 is preferably flexible. For example, in an embodiment, the body portion 10 may include a contoured or ribbed cross-section so as to have the form of a flexible or expandable bellows. In the embodiment shown, this bellows-type arrangement includes one or more concentric annular grooves 9 along the inner and outer wall of the body portion 10. These concentric annular grooves 9 allow the body portion 10 to absorb forces and torques applied to the seal device 100. This allows for the body portion 10 to be deflected, if necessary, e.g., when an instrument is inserted or moved off-axis into or within the device, with a minimal effect on the opening of a slit 13 through which an instrument is passed.

In an embodiment, as shown in FIG. 2, gussets 11 are employed on the outside of the slit 13 and assist with biasing the slit 13 into a closed position in the absence of an inserted instrument. The gussets 11 may be located at any position around the slit 13. In the embodiment shown, the gussets 11 are located on opposite sides of the slit 13 and adjacent to respective ends of the slit 13. Providing the gussets 13 adjacent to the ends of the slit 13 has the added benefit that, when an instrument is in place within the slit 13, the gussets 11 will provide a greater biasing of end regions of the slit 13, thereby reducing the leakage through these end regions of the slit 13.

In an embodiment, ramps 12 may be located on respective ones of the interior surfaces of the conical body portion 20 of the seal device 100 near slit 13. The ramps 12 may serve as lead-ins, whereby an inserted instrument contacts the ramps 12 prior to contacting the material that forms the slits 13. In this manner, an inserted instrument is less likely to contact the material of the slit 13 and thereby is less likely to damage such material.

Furthermore, the seal device 100 can be made from a variety of materials having elastic or compliant properties, including, but not limited to elastomers such as cellular rubbers, natural rubbers, and synthetic rubbers. Alternatively, the material may comprise a viscoelastic gel. In another embodiment, a flexible casing containing a predetermined quantity of fluid may be used. Optionally, a fabric material, such as SPANDEX containing a mixture of LYCRA and NYLON can be superposed upon the seal device 100 to minimize the potential of piercing, penetrating or tearing of the resilient material by the instrument.

Additionally, the seal device 100 can be coated or impregnated with a therapeutic agent or material, such as an oligodynamic metal or an antimicrobial medium.

It will be understood by those skilled in the art that various modifications and changes in form and detail may be made therein without departing from the scope and spirit of the present disclosure. Accordingly, modifications such as those suggested above, but not limited thereto, are to be considered within the scope of the disclosure. Therefore, the above description should not be construed as limited to the disclosed embodiments. Other embodiments within the scope and spirit of the present disclosure will appear to those skilled in the art.

What is claimed is:

1. A seal device, comprising:
    a hollow body portion defining a generally conical section and a distal section extending substantiality longitudinally from the generally conical section, the distal section including a distal end and interior surfaces, the interior surfaces substantially parallel with respect to one another, the interior surfaces configured and adapted to contact a surgical instrument inserted therebetween, the distal end defining an elongated slit having a first end, a second end, and a midpoint centered between the first and second ends, the elongated slit defining a lumen extending through the distal section; and
    a first pair and a second pair of diametrically opposed gussets located on the exterior surface of the body portion, the first pair of gussets disposed between the first end and the midpoint of the elongated slit, the second pair of gussets disposed between the second end and the midpoint of the elongated slit.

2. The seal device of claim 1, wherein the gussets help bias the slit into a closed position in the absence of an instrument.

3. The seal device of claim 1, wherein the gussets help bias the ends of the slit towards a closed position when an instrument is present in the slit.

4. The seal device of claim 1, wherein the body portion has a proximal end, the proximal end including an instrument seal.

5. The seal device of claim 4, wherein the instrument seal is fitted within the proximal end of the body portion.

6. The seal device of claim 1, wherein the body portion includes a flexible portion.

7. The seal device of claim 6, wherein the flexible portion includes a bellows-type arrangement.

8. The seal device of claim 6, wherein the flexible portion includes a series of concentric annular grooves in a wall of the body portion.

9. The seal device of claim 1, wherein the gussets bias the slit towards a closed position in the absence of an inserted instrument.

10. The seal device of claim 1, wherein the gussets inhibit leakage through the elongated slit when the surgical instrument is positioned within the elongated slit.

* * * * *